US011298331B2

(12) United States Patent
Lindenblatt et al.

(10) Patent No.: US 11,298,331 B2
(45) Date of Patent: Apr. 12, 2022

(54) SOLID PHARMACEUTICAL PREPARATION CONTAINING LEVOTHYROXINE

(71) Applicant: MERCK PATENT GMBH, Darmstadt (DE)

(72) Inventors: Hiltrud Lindenblatt, Egelsbach (DE); Thomas T. Frank, Weiterstadt (DE); Reiner Vonderschmitt, Ober-Ramstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 281 days.

(21) Appl. No.: 15/645,436

(22) Filed: Jul. 10, 2017

(65) Prior Publication Data

US 2017/0304246 A1 Oct. 26, 2017

Related U.S. Application Data

(63) Continuation of application No. 14/422,546, filed as application No. PCT/EP2013/002293 on Aug. 1, 2013, now abandoned.

(30) Foreign Application Priority Data

Aug. 20, 2012 (EP) .................... 12005960

(51) Int. Cl.
*A61K 31/198* (2006.01)
*A61K 47/12* (2006.01)
*A61K 9/48* (2006.01)
*A61K 31/195* (2006.01)
*A61K 9/20* (2006.01)
*A61K 9/16* (2006.01)
*A61K 9/28* (2006.01)
*A61K 9/50* (2006.01)

(52) U.S. Cl.
CPC .......... *A61K 31/198* (2013.01); *A61K 9/1623* (2013.01); *A61K 9/1652* (2013.01); *A61K 9/1658* (2013.01); *A61K 9/2077* (2013.01); *A61K 9/28* (2013.01); *A61K 9/4858* (2013.01); *A61K 9/50* (2013.01); *A61K 31/195* (2013.01); *A61K 47/12* (2013.01)

(58) Field of Classification Search
CPC .. A61K 31/198; A61K 9/1623; A61K 9/1652; A61K 9/1658; A61K 9/2077; A61K 9/28; A61K 9/4858; A61K 9/50; A61K 31/195; A61K 47/12; A61P 5/00; A61P 5/14; A61P 35/00

See application file for complete search history.

(56) References Cited

U.S. PATENT DOCUMENTS

| 5,753,254 | A | 5/1998 | Khan et al. |
| 5,958,979 | A | 9/1999 | Wolfgang |
| 6,017,958 | A * | 1/2000 | Kun ............... A61K 31/166 514/532 |
| 6,646,007 | B1 * | 11/2003 | Schreder ......... A61K 9/2063 514/567 |
| 6,649,186 | B1 | 11/2003 | Robinson |
| 7,052,717 | B2 * | 5/2006 | Hanshew, Jr. ..... A61K 9/2013 424/464 |
| 8,008,349 | B2 | 8/2011 | Schreder et al. |
| 2004/0013725 | A1 * | 1/2004 | Hanshew, Jr. ..... A61K 9/2013 424/465 |
| 2004/0063611 | A1 | 4/2004 | Schreder et al. |
| 2007/0014851 | A1 | 1/2007 | Burghart |
| 2010/0247637 | A1 | 9/2010 | Zoppetti et al. |
| 2011/0206775 | A1 * | 8/2011 | Groenewoud ...... A61K 9/2054 424/568 |

FOREIGN PATENT DOCUMENTS

| AU | 2004234176 B2 | 5/2010 | |
| CN | 1301148 A | 6/2001 | |
| DE | 19541128 C2 | 11/1997 | |
| TW | 561058 B | 11/2003 | |
| WO | 9520953 A1 | 8/1995 | |
| WO | 9520954 A1 | 8/1995 | |
| WO | WO-9520954 A1 * | 8/1995 | ........... A61K 9/0056 |
| WO | 9959551 A1 | 11/1999 | |
| WO | 2004096177 A1 | 11/2004 | |
| WO | 2010108553 A1 | 9/2010 | |

OTHER PUBLICATIONS

Collier et al., AAPS PharmSciTech 11: 818 (2010) (Year: 2010).*
The Merck Index entry for thyroxine (Year: 2017).*
Patel et al., Int J Pharmaceutics 264: 35-43 (2003) (Year: 2003).*
Patel et al., Int J Pharm 264: 35-43 (2003). (Year: 2003).*
The Merck Index entry for thyroxine (2018) (Year: 2018).*
International Search Report for PCT/EP2013/002293 dated Jan. 30, 2014.
English Abstract of WO2004096177, Publication Date: Nov. 11, 2004.
Patel H. et al: The effect of excipients on stability of levothyroxine sodium pentahydrate tablets, Int J Pharm 264 (2003) 35-43.

* cited by examiner

*Primary Examiner* — Monica A Shin
(74) *Attorney, Agent, or Firm* — Millen, White, Zelano and Branigan, P.C.; Harry Shubin

(57) ABSTRACT

The invention relates to a solid pharmaceutical preparation comprising levothyroxine sodium, gelatine, citric acid and a filler. The solid pharmaceutical preparation has an improved stability.

18 Claims, No Drawings

SOLID PHARMACEUTICAL PREPARATION CONTAINING LEVOTHYROXINE

The invention relates to a solid pharmaceutical preparation comprising levothyroxine sodium, gelatine, citric acid and a filler. The solid pharmaceutical preparation has an improved stability.

Levothyroxine sodium is used to treat thyroid hormone deficiency, and occasionally to prevent the recurrence of thyroid cancer. In treatment of thyroid hormone deficiency very low daily doses of levothyroxine sodium are used in the range from 25 to 300 μg. Due to its high potency it is very important to avoid dosage variations as this may cause serious symptoms of hypothyroidism such as as severe depression, fatigue, weight gain, constipation, cold intolerance, swelling, and difficulty concentrating, if levothyroxine sodium is underdosed, or of hypothyroidism, such as pain, heart palpitations, or cardiac arrhythmias, if levothyroxine sodium dosis is too high. Therefore, storage stability of pharmaceutical preparations containing levothyroxine sodium is a critical issue.

DE 195 41 128 teaches to stabilize thyroxine preparations by addition of sodium thiosulfate. However, the use of substances like sodium thiosulfate in pharmaceutical preparations is undesirable from the toxicological point of view.

WO 2004/096177 A1 teaches to stabilize pharmaceutical preparations containing levothyroxine sodium by providing them with a water activity below 0.4. Disadvantageously the water activity of the formulations varies with the change of relative humidity during shelf life so that additional measures have to be taken such as moisture-tight packs, which result in additional costs and waste management problems.

Patel et al. examined the effect of various pH modifying additives on the stability of levothyroxine sodium tablets (Patel H. et al: The effect of excipients on stability of levothyroxine sodium pentahydrate tablets, Int J Pharm 264 (2003) 35-43). It was found that the basic pH modifying additives sodium carbonate, sodium bicarbonate and magnesium oxide lead to improvement of the stability of levothyroxine sodium tablets whereas acid pH modifying additives tartaric acid and citric acid lead to impairment of stability.

WO 99/59551 A1 teaches that storage stability of levothyroxine sodium containing solid pharmaceutical preparations can be improved by using gelatine as a binder. As described in the introduction such stabilized formulation has been developed in order to meet the increased requirements on stability as established by the Food and Drug Administration (FDA) in 1996. According to such FDA requirements levothyroxine sodium degradation in tablets throughout their shelf life has been fixed to 10% at the most.

In 2007 the FDA has raised its requirements on stability of levothyroxine sodium containing products to further diminish the risk caused this. In fact the limit of levothyroxine sodium degradation in tablets was lowered from 10 to 5% (FDA press release from 3 Oct. 2007).

There is an ongoing demand for pharmaceutical preparations having an improved stability. The pharmaceutical preparations should ensure release of active compound in accordance with the requirements, should not comprise any toxicologically unacceptable adjuvants and should be capable of storage in a stable manner over an extended time.

Surprisingly, it has been found that a solid pharmaceutical preparation which meets these requirements and has an improved storage stability can be provided if it comprises besides levothyroxine sodium, gelatine, citric acid and a filler. Therefore, when an object of the present invention is directed to a solid pharmaceutical preparation comprising levothyroxine sodium, gelatine, citric acid and a filler.

The improved stability of a solid pharmaceutical preparation is especially surprising in view of that the prior art teaching of Patel et al. (as cited above) according to which the addition of citric acid leads not only to no improvement but even to a deterioration of levothyroxine sodium in tablets.

U.S. Pat. No. 6,649,186 B1 disclose effervescent granules which are prepared by hot melt extruding which may contain levothyroxine sodium. Such effervescent granules contain an acid component such as citric acid together with a basic component such as sodium carbonate or sodium bicarbonate which upon contact with water react under carbon dioxide development. The pharmaceutical preparation of the present invention is preferably not an effervescent preparation. Therefore, a further object of the present invention is directed to a solid pharmaceutical preparation, which is characterized in that it is not an effervescent preparation.

U.S. Pat. No. 5,753,254 A discloses a solid fast dispersing dosage form containing thyroid hormone which may also comprise citric acid to induce the formation of saliva. Solid fast dispersing dosage forms are oral administration forms which disintegrate readily and quickly in the mouth within seconds upon contact with saliva when taken orally. The pharmaceutical preparation of the present invention is preferably not a solid fast dispersing dosage form. Therefore, a further object of the invention is directed to a solid pharmaceutical preparation, which is characterized in that it is not a solid fast dispersing dosage form.

According to an appropriate embodiment of the invention solid pharmaceutical preparation contains 5 to 400 μg, preferably 10 to 300 μg, in particular 25 to 300 μg, of levothyroxine sodium. Preferably the solid pharmaceutical preparation contain 25, 50, 75, 88, 100, 112, 125, 137, 150, 175, 200 or 300 μg of levothyroxine sodium.

If levothyroxine sodium is present in micronized form, especially with a particle size from 5 μm to 25 μm, the dissolution of the solid pharmaceutical preparation improves. Therefore, a preferred object of the present invention is directed to a solid pharmaceutical preparation, which is characterized in that it contains levothyroxine sodium micronized with a particle size from 5 μm to 25 μm.

According to an appropriate embodiment of the present invention gelatine is present in the solid pharmaceutical preparation in an amount from 0.5 to 20% by weight, preferably from 1 to 10% by weight, particularly preferably from 2 to 10% by weight, most preferably at about 5%.

According to a further appropriate embodiment of the present invention citric acid is present in the solid pharmaceutical preparation in an amount from 0.1 to 5% by weight, preferably from 0.2 to 3% by weight, particularly preferably from 0.4 to 2% by weight.

According to a preferred embodiment of the invention the pharmaceutical preparation comprises besides levothyroxine sodium liothyronine sodium a as further active ingredient. Therefore, the invention is also directed to a solid pharmaceutical preparation, which is characterized in that it comprises liothyronine sodium.

A filler is an agent increasing the bulk of the pharmaceutical preparation by providing the quantity of material which is needed to form such pharmaceutical preparation. The filler being present in the solid preparation of the present invention is preferably a sugar alcohol, a sugar, a starch, a cellulose or a mixture thereof.

Sugar alcohol is taken to mean a monosaccharide whose reactive carbonyl group has been reduced to the alcohol group, such as, for example, a hexitol or a pentitol. The solid preparation according to the invention preferably comprises hexitols, such as, for example, mannitol, sorbitol, dulcitol, xylitol or ribitol, as sugar alcohol. Particular preference is given to the presence of mannitol and/or sorbitol, most particular preference is given to mannitol.

Sugar is taken to mean a monosaccharide such as, for example, a hexitol or a pentitol and a disaccharide consisting of two monosaccharides joined by a glycosidic bond. The solid preparation according to the invention preferably comprises glucose, fructose or mannose, as a monosaccharide or lactose, saccharose or maltose, as a disaccharide. Particular preference is given to lactose.

Starch is taken to mean a polysaccharide comprising helical amylose and branched amylopectin, it is produced by green plants such as potatoes, wheat, maize, rice, and cassava. The solid preparation according to the invention preferably comprises potato starch, rice starch, maize starch or precooked starch, i.e. pregelatinized starch. Particular preference is given to maize starch and pregelatinized starch, most particular preference is given to maize starch.

Cellulose is taken to mean a polysaccharide consisting of a linear chain of several hundred to over ten thousand β(1→4) linked D-glucose. The solid preparation according to the invention preferably comprises powdered cellulose or microcrystalline cellulose, particular preferred is microcrystalline cellulose.

According to an appropriate embodiment of the present invention the solid pharmaceutical preparation is characterized in that the filler is a sugar alcohol such as sorbitol or mannitol dulcitol, xylitol or ribitol, preferably sorbitol or mannitol, particular preferably mannitol, a sugar such as glucose, fructose, mannose, lactose, saccharose or maltose, preferably lactose, saccharose or maltose, particular preferably lactose, a starch such as potato starch, rice starch, maize starch or pregelatinized starch, preferably maize starch or pregelatinized starch, particular preferably maize starch, a cellulose such as powdered cellulose or microcrystalline cellulose, preferably microcrystalline cellulose, or a mixture thereof.

According to a particularly preferred embodiment of the present invention solid pharmaceutical preparation is characterized in that the filler is mannitol and/or maize starch.

According to a appropriate embodiment of the present invention the filler is present in the solid pharmaceutical preparation in an amount from 70 to 98% by weight, preferably 80 to 98% by weight, particular preferably 85 to 95% by weight.

The stability of the solid pharmaceutical preparation can be further improved if it comprises an antioxidant selected from the group consisting of tocopherol, sodium ascorbate, propyl gallate, tertiary butylhydroquinone, butylated hydroxyanisole and butylated hydroxytoluene (BHT), preferably butylated hydroxyanisole or butylated hydroxytoluene, particular preferably butylated hydroxytoluene. Therefore, a preferred object of the invention is directed to a solid pharmaceutical preparation, which is characterized in that it further comprises an antioxidant selected from the group consisting of tocopherol, propyl gallate, tertiary butylhydroquinone, butylated hydroxyanisole and butylated hydroxytoluene, preferably hydroxyanisole or butylated hydroxytoluene, particular preferably butylated hydroxytoluene. The solid pharmaceutical preparation according to the invention comprises 0.01 to 2% by weight, preferably 0.05 to 0.5% by weight, particularly preferably 0.08 to 0.2 and most preferably 0.1%-0.15% by weight of the antioxidant.

The solid pharmaceutical preparation can be in granule, pellet, capsule or tablet form. While capsules and tablets provide the amount of active compound intended to be taken in each case as a clearly defined individual dose, the amount of active compound required in each case can be adapted in a simple manner by means of pellets and granules.

Granules can be prepared by granulation. Pellets are solid, small, spherical medicament forms, such as, for example, granule grains or microtablets, having a very narrow particle-size range. Granules and pellets represent an independent medicament form, but can also serve as intermediate product for the production of tablets. If it is intended that predetermined amounts of active compound can be administered by means of granules or pellets, these are, in order to ensure adequate dosage accuracy, also provided as portioned granules or introduced into capsules. The solid pharmaceutical preparation according to the invention is preferably in granule, pellet, capsule or tablet form, particular preferably in capsule or tablet form, very particular preferably in tablet form.

Therefore, a further object of the present invention is directed to a solid pharmaceutical preparation, which is characterised in that it is in granule, pellet, capsule or tablet form, particular preferably in capsule or tablet form. A very particularly preferred object of the present invention is directed to a solid pharmaceutical preparation, which is characterized in that it is a tablet.

The solid pharmaceutical preparation may contain a disintegrating agent in order to shorten the disintegration time of the tablet or granules, enabling the active compound to be released rapidly from the it. Therefore, a further object of the present invention is directed to a solid pharmaceutical preparation, which is characterised in that a disintegrating agent is present.

Appropriate disintegrating agent in the solid pharmaceutical preparation of the present invention are sodium starch glycolate, carboxymethylcellulose sodium, crosslinked carboxymethylcellulose sodium or a mixture thereof.

Therefore, a further object of the present invention is directed to a solid pharmaceutical preparation which is characterized in that the disintegrating agent is sodium starch glycolate or carboxymethylcellulose sodium or a mixture thereof.

A preferred embodiment of the solid pharmaceutical preparation comprises as a disintegrating agent carboxymethylcellulose sodium, particular preferably crosslinked carboxymethylcellulose sodium. Accordingly, a preferred object of the present invention is directed to a solid pharmaceutical preparation which is characterized in that disintegrating agent is carboxymethylcellulose sodium, particular preferably crosslinked carboxymethylcellulose sodium.

Depending on the nature of the disintegrating agent, this may be present in the solid preparation according to the invention in a proportion by weight of 0.01 to 20% by weight. The solid preparation according to the invention preferably comprises 0.1 to 10% by weight, particularly preferably 1-5% by weight, of the disintegrating agent.

According to an appropriate embodiment of the invention the solid pharmaceutical preparation comprises 1 to 10% by weight of gelatine, 0.1 to 3% by weight citric acid, 50 to 80% by weight of mannitol or lactose and 10 to 30% by weight of maize starch. Therefore, a further object of the present invention is directed to a solid pharmaceutical preparation, which is characterised in that it comprises 1 to 10% by weight of gelatine, 0.1 to 3% by weight citric acid, 50 to 80% by weight of mannitol or lactose, 10 to 30% by weight maize starch.

According to an preferred embodiment of the invention the solid pharmaceutical preparation comprises 0,05 to 0,5% by weight butylated hydroxytoluene. Therefore, a further object of the present invention is directed to a solid pharmaceutical preparation, which is characterised in that it comprises 0,05 to 0,5% by weight butylated hydroxytoluene. Preferably the 0,05 to 0,5% by weight butylated hydroxytoluene are is present in the solid pharmaceutical preparation, which is characterised in that it comprises 1 to 10% by weight of gelatine, 0.1 to 3% by weight citric acid, 50 to 80% by weight of mannitol or lactose, 10 to 30% by weight maize starch.

A particular preferred object of the invention is directed to a solid pharmaceutical preparation which is characterised in that it comprises 2 to 8% by weight of gelatine, 0.5 to 2% by weight citric acid, 60 to 75% by weight of mannitol or lactose, 15 to 25% by weight of maize starch and optionally 0,08 to 0,2% by weight butylated hydroxytoluene.

If the solid pharmaceutical preparation according to the invention is a tablet, this may also comprise lubricants in order to reduce the sliding friction of the tableting material and ram in the mould during the tableting operation and to prevent sticking to the rams. Suitable lubricants are alkaline-earth metal salts of fatty acids, such as magnesium stearate or calcium stearate, fatty acids, such as stearic acid, higher fatty alcohols such al cetyl alcohol or stearyl alhohol, fats such as glyceryl dipalmitostearate, glyceryl distearate, stearin or glyceryl dibehenate, alkaline-earth metal salts of $C_{16}$-$C_{18}$ alkyl substituted dicarbonic acids such as sodium stearyl fumarate, hydrated vegetable oils such as hydrated castor oil or hydrated cotton seed oil, or minerals such as silica or talc. The solid preparation according to the invention preferably comprises magnesium stearate, stearic acid or sodium stearyl fumarate as lubricant, particular preferably magnesium stearate. Lubricants are preferably present in the solid preparation according to the invention in a proportion of 0.1 to 5% by weight, preferably 0.25 to 4% by weight, particularly preferably 0,5 to 3% by weight, most preferably about 1% by weight.

The solid preparation according to the invention can be prepared by methods known to the person skilled in the art.

Granules are produced by granulation, which can basically be carried out by the moist or dry route. In the case of moist granulation, for example, a granulation liquid, which preferably comprises a binder, is added to a powder mixture comprising the active compound together with the sugar alcohol and any further suitable adjuvants, the mixture is converted into aggregates of suitable size (granules) and subsequently dried. The active compound can also be introduced into the granules by suspension in the granulation liquid. The conversion of the powder mixture into aggregates of suitable size can be carried out, for example, by so-called build-up granulation, for example in coating pans, by means of plate granulation or in fluidised-bed methods, for example by the Glatt or Wurster method, or by so-called reduction granulation, in which the powder mixture is firstly moistened and converted into a plastically mouldable mass and subsequently converted into aggregates of the desired size, for example by extrusion through a screen having meshes of suitable size. In the case of dry granulation, the powder mixture is pressed, for example, by means of compaction between two counter-rotating compaction rolls to give flakes, which are subsequently comminuted to give granules.

Pellets can be produced by granulation and subsequent rounding-off (spheronisation), for example by means of plate granulation, or alternatively by pressing powders or granules to give microtablets.

The preparation according to the invention in the form of tablets can be produced by pressing powder mixtures (direct compression) or by pressing granules. In the simplest case of direct compression, the active compound is firstly mixed with the excipients and the resultant powder mixture is pressed directly to give the solid preparation according to the invention.

According to a preferred embodiment of the invention the solid pharmaceutical preparation is prepared by a process, which is characterized in that
(a) levothyroxine sodium and optionally liothyronine sodium is/are suspended in an aqueous gelatine solution,
(b) the suspension obtained by step (a) is sprayed onto the filler in a fluidized bed granulation and dried to form granules,
(c) the granules obtained by step (b) are collected and optionally,
(d) a disintegrant and optionally a lubricant is/are mixed with the granules obtained by step (c), and
(e) the mixture obtained by step (d) is compressed to give tablets.

Accordingly, one object of the present invention is further directed to a process for the production of a solid pharmaceutical preparation, which is characterized in that
(a) levothyroxine sodium and optionally liothyronine sodium is/are suspended in an aqueous gelatine solution,
(b) the suspension obtained by step (a) is sprayed onto the filler in a fluidized bed granulation and dried to form granules,
(c) the granules obtained by step (b) are collected and optionally,
(d) a disintegrant and optionally a lubricant is/are mixed with the granules obtained by step (c), and
(e) the mixture obtained by step (d) is compressed to give tablets.

The granules obtained by performing the steps (a) to (c) can be directly used as a medicament form without performing the optional steps (d) and (e). If the granules are used they can be provided as portioned granules or introduced into capsules to ensure adequate dosage accuracy as described above.

According to a further appropriate embodiment of the invention the solid pharmaceutical preparation is prepared by a process, which is characterized in that citric acid and, if present, the antioxidant is dissolved in in the aqueous gelatine solution used in step (a) or is admixed with the granules in step (d). Therefore, a further object of the invention is directed to a process for the production of a solid pharmaceutical preparation, which is characterized in that citric acid and, if present, the antioxidant is dissolved in the aqueous gelatine solution used in step (a) or is admixed with the granules in step (d).

According to an appropriate embodiment of the invention the granules or the tablets are provided with a coating. Therefore, a further object of the invention is directed to a process for the production of a solid pharmaceutical preparation, which is characterized in that the granules or the tablets are provided with a coating.

Suitable coatings are film-forming polymers, such as, for example, those from the group of the cellulose derivatives, dextrins, starches, natural gums, such as, for example, gum arabic, xanthans, alginates, polyvinyl alcohol, polymethacrylates and derivatives thereof, such as, for example, eudragites, which may be applied to the tablet as solutions or suspensions by means of the various pharmaceutical conventional methods, such as, for example, film coating. Use is usually made here of solutions/suspensions which, besides the film-forming polymer, also comprise further adjuvants, such as hydrophilisers, plasticisers, surfactants, dyes and white pigments, such as, for example, titanium dioxide.

The examples illustrate the invention without being restricted thereto.

EXAMPLE 1

Tablet (batch 015093) comprising
0.075 mg of levothyroxine sodium
68.525 mg of mannitol
20.00 mg of maize starch
5.00 mg of sodium starch glycolate
5.00 mg of gelatine
0.40 mg of citric acid
1.00 mg of magnesium stearate The gelatin is diluted in hot water (ca. 90% of total amount of water, temperature 90° C.±10° C.) under stirring. The levothyroxine sodium is suspended in cold water (10% of total amount of water) with Ultraturrax. When the gelatin solution has cooled down to 50° C.±5° C., the levothyroxine sodium suspension is given to it, while the final temperature of the granulation fluid is 40-45° C.

The granulation fluid containing gelatin and active compound is sprayed onto the mannitol and maize starch in the fluidised bed. The temperature of the granulation fluid is kept at around 40° C. The granules are finalized as soon a outlet air temperature has raised up to 40° C.

Citric acid, sodium starch glycolate and magnesium stearate are admixed with the granules, the resultant mixture is pressed to give tablets. Instead of admixing with the granules citric acid can also be added by dissolving it during preparation of the levothyroxine sodium containing gelatine solution.

EXAMPLE 2

Tablet (batch 015099) comprising
0.30 mg of levothyroxine sodium
68.20 mg of mannitol
20.00 mg of maize starch
3.50 mg of croscarmellose sodium
5.00 mg of gelatine
2.00 mg of citric acid
1.00 mg of magnesium stearate
The tablets are produced analogous to Example 1.

EXAMPLE 3

Tablet (batch 014916) comprising
0.105 mg of levothyroxine sodium
70.295 mg of mannitol
20.00 mg of maize starch
3.50 mg of croscarmellose sodium
5.00 mg of gelatine
0.10 mg of butylated hydroxytoluene
0.80 mg of citric acid
1.00 mg of magnesium stearate
The tablets are produced analogous to Example 1. The butylated hydroxytoluene is diluted in hot water (ca. 90% of total amount of water, temperature 90° C.±10° C.) under stirring. Afterwards the gelatin is given to this solution under stirring. The Levothyroxine sodium is suspended in cold water (10% of total amount of water) with Ultraturrax. As soon the BHT-gelatin solution has cooled down to 50° C.±5° C., the levothyroxine sodium suspension is given to it, while the final temperature of the granulation fluid now is 40-45° C.

EXAMPLE 4

Tablet comprising
0.300 mg of levothyroxine sodium
73.100 mg of mannitol
20.00 mg of maize starch
3.50 mg of croscarmellose sodium
2.00 mg of gelatine
0.10 mg of butylated hydroxytoluene
0.80 mg of citric acid
1.00 mg of magnesium stearate
The tablets are produced analogous to Example 3.

EXAMPLE 5

Tablet comprising
0.025 mg of levothyroxine sodium
65.375 mg of mannitol
20.00 mg of maize starch
3.50 mg of croscarmellose sodium
10.00 mg of gelatine
0.10 mg of butylated hydroxytoluene
0.80 mg of citric acid
1.00 mg of magnesium stearate
The tablets are produced analogous to Example 3.

EXAMPLE 6

Tablet comprising
0.105 mg of levothyroxine sodium
70.395 mg of isomalt
20.00 mg of maize starch
3.50 mg of croscarmellose sodium
5.00 mg of gelatine
0.40 mg of citric acid
1.00 mg of magnesium stearate
The tablets are produced analogous to Example 1.

EXAMPLE 7

Tablet comprising
0.105 mg of levothyroxine sodium
81.645 mg of cellulose microcrystalline
3.50 mg of croscarmellose sodium
4.50 mg of gelatine
1.50 mg of citric acid
0.25 mg of magnesium stearate
The tablets are produced analogous to Example 1.

EXAMPLE 8

Tablet comprising
0.105 mg of levothyroxine sodium
70.295 mg of sorbitol
20.00 mg of maize starch
3.50 mg of croscarmellose sodium
5.00 mg of gelatine
0.10 mg of butylated hydroxytoluene 0.80 mg of citric acid
1.00 mg of magnesium stearate
The tablets are produced analogous to Example 3.

EXAMPLE 9

Tablet comprising
0.105 mg of levothyroxine sodium
70.295 mg of sucrose
20.00 mg of maize starch
3.50 mg of croscarmellose sodium
5.00 mg of gelatine
0.10 mg of butylated hydroxytoluene
0.80 mg of citric acid
1.00 mg of magnesium stearate
The tablets are produced analogous to Example 3.

EXAMPLE 10

Tablet comprising
0.105 mg of levothyroxine sodium
70.395 mg of mannitol
20.00 mg of maize starch
3.50 mg of croscarmellose sodium
5.00 mg of gelatine
2.00 mg of citric acid
0.10 mg of sodium ascorbate
1.00 mg of magnesium stearate
The tablets are produced analogous to Example 1.

EXAMPLE 11

Granules comprising
0.105 mg of levothyroxine sodium
70.295 mg of mannitol
20.00 mg of maize starch
5.00 mg of gelatine
0.10 mg of butylated hydroxytoluene
0.80 mg of citric acid The citric acid and the gelatin are diluted in hot water (ca. 90% of total amount of water, temperature 90° C.±10° C.) under stirring. The levothyroxine sodium is suspended in cold water (10% of total amount of water) with Ultraturrax. When the gelatin solution with the citric acid has cooled down to 50° C.±5° C., the levothyroxine sodium suspension is given to it, while the final temperature of the granulation fluid is 40-45° C.

The granulation fluid containing gelatin and active compound is sprayed onto the mannitol and maize starch in the fluidised bed. The temperature of the granulation fluid is kept at around 40° C. The granules are finalized as soon a outlet air temperature has raised up to 40° C.

EXAMPLE 12

Capsules comprising granules
Granules of example 11 filled into capsules (gelatine or HPMC)

COMPARISON EXAMPLE 1

Tablet (batch 127494) comprising
0.105 mg of levothyroxine sodium
65.895 mg of lactose
25.00 mg of maize starch
3.50 mg of crosscarmellose sodium
5.00 mg of gelatine
0.50 mg of magnesium stearate
The tablets are produced analogous to Example 1.

COMPARISON EXAMPLE 2

Tablet (batch 014698) comprising
0.105 mg of levothyroxine sodium
70.395 mg of mannitol
20.00 mg of maize starch
3.50 mg of crosscarmellose sodium
5.00 mg of gelatine
0.50 mg of magnesium stearate
The tablets are produced analogous to Example 1.

COMPARISON EXAMPLE 3

Tablet (batch 014842) comprising
0.105 mg of levothyroxine sodium
70.295 mg of mannitol
20.00 mg of maize starch
3.50 mg of crosscarmellose sodium
5.00 mg of gelatine
0.10 mg of butylated hydroxytoluene
1.00 mg of magnesium stearate
The tablets are produced analogous to Example 1. Butylated hydroxytoluene was admixed as described in Example 3.

Stability Testing

To assess the influence of the ingredients, especially citric acid and/or antioxidant on storage stability the pharmaceutical preparations of Examples 1 to 4 and the Comparison Examples 1 and 2 were transferred into glass bottles without closure and stored under elevated temperature and humidity (60 degree Celsius and 75% relative humidity (r.h.)). Storage times and the amounts of active compound measured in each case are shown in Table 1.

TABLE 1

| Example | Day | Levothyroxine Sodium [µg] | Levothyroxine Sodium [%] |
|---|---|---|---|
| Preparation with citric acid | | | |
| Ex. 1 | 0 | 99.4 | 100 |
| Ex. 1 | 14 | 90.2 | 90.7 |
| Preparation with citric acid | | | |
| Ex. 2 | 0 | 103.5 | 100 |
| Ex. 2 | 14 | 94.8 | 91.6 |
| Preparation with citric acid and butylated hydroxytoluene | | | |
| Ex. 3 | 0 | 103.7 | 100 |
| Ex. 3 | 14 | 96.4 | 93.0 |
| Preparation without citric acid and butylated hydroxytoluene | | | |
| Comp. Ex. 1 | 0 | 105.2 | 100 |
| Comp. Ex. 1 | 14 | 70 | 66.5 |
| Preparation without citric acid and butylated hydroxytoluene | | | |
| Comp. Ex. 2 | 0 | 106.8 | 100 |
| Comp. Ex. 2 | 14 | 93.9 | 87.9 |
| Preparation without citric acid but with butylated hydroxytoluene | | | |
| Comp. Ex. 3 | 0 | 105.5 | 100 |
| Comp. Ex. 3 | 14 | 93.6 | 88.7 |

As demonstrated by the data in table 1 the presence of citric acid leads to an improvement of stability which is further improved by the antioxidant. As no improvement of stability is obtained if the antioxidant is present without citric acid the antioxidant exhibits an antioxidant unexpectedly exhibits a synergistic stabilization effect in combination with citric acid.

The pharmaceutical preparations of Examples 3 and 4 and Comparison Examples were transferred into HDPE bottles, closed and stored at 40° C. and 75% r.h. Storage times and the amounts of active compound measured in each case are shown in Table 2.

TABLE 2

| Example | Weeks | Levothyroxine Sodium [μg] | Levothyroxine Sodium [%] |
|---|---|---|---|
| Preparation with citric acid and butylated hydroxytoluene | | | |
| Ex. 4 | 0 | 103.7 | 100 |
| Ex. 4 | 13 | 103.7 | 100 |
| Ex. 4 | 26 | 103.6 | 99.9 |
| Preparation without citric acid and butylated hydroxytoluene | | | |
| Comp. Ex. 1 | 0 | 104.5 | 100 |
| Comp. Ex. 1 | 13 | 102.2 | 97.8 |
| Comp. Ex. 1 | 26 | 101.4 | 97.0 |
| Preparation without citric acid and butylated hydroxytoluene | | | |
| Comp. Ex. 2 | 0 | 105.5 | 100 |
| Comp. Ex. 2 | 13 | 102.9 | 97.5 |
| Comp. Ex. 2 | 26 | 101.1 | 95.8 |
| Preparation without citric acid but with butylated hydroxytoluene | | | |
| Comp. Ex. 3 | 0 | 105.5 | 100 |
| Comp. Ex. 3 | 13 | 102.0 | 96.7 |
| Comp. Ex. 3 | 26 | 101.8 | 96.5 |

As apparent from table 2 the presence of an antioxidant does not exhibit a significant stabilisation effect without the presence of citric acid. Further and surprisingly the combination of citric acid with the antioxidant leads to such a good stabilization effect that after half year storage at elevated temperature and humidity (40° C. and 75% r.h.) the content of levothyroxine sodium in the preparation decreased only 0.1% by weight.

Analytical Test Methods:

Identity, purity and assay of the solid pharmaceutical preparation comprising levothyroxine sodium are tested by high-performance liquid chromatography or ultra high performance liquid chromatography with UV detection using an reversed phase column and a gradient system after preparation and during the stability studies. The extraction medium and mobile phase used are mixtures of acetonitrile, water and phosphoric acid.

The invention claimed is:

1. A solid pharmaceutical preparation comprising levothyroxine sodium, 2-10% by weight based on the preparation of gelatine, 0.2 to 3% by weight based on the preparation of citric acid, and a filler that is 50 to 80% by weight, based on the preparation, of mannitol, sucrose or lactose, and 10 to 30% by weight, based on the preparation, of maize starch.

2. The solid pharmaceutical preparation according to claim 1, further comprising liothyronine sodium.

3. The solid pharmaceutical preparation according to claim 1, wherein the filler is sucrose.

4. The solid pharmaceutical preparation according to claim 1, wherein filler is mannitol and maize starch.

5. The solid pharmaceutical preparation according to claim 1, further comprising an antioxidant that is tocopherol, propyl gallate, tertiary butylhydroquinone, butylated hydroxyanisole or butylated hydroxytoluene.

6. The solid pharmaceutical preparation according to claim 5, wherein the antioxidant is butylated hydroxyanisole or butylated hydroxytoluene.

7. The solid pharmaceutical preparation according to claim 1, in granule, pellet, capsule or tablet form.

8. The solid pharmaceutical preparation according to claim 7, that is a tablet.

9. The solid pharmaceutical preparation according to claim 1, wherein at least one disintegrating agent is present.

10. The solid pharmaceutical preparation according to claim 9, wherein the disintegrating agent is sodium starch glycolate, carboxymethylcellulose sodium or a mixture thereof.

11. The solid pharmaceutical preparation according to claim 10, wherein the disintegrating agent present is carboxymethylcellulose sodium.

12. The solid pharmaceutical preparation according to claim 1, comprising 0.05 to 0.5% by weight butylated hydroxytoluene.

13. The solid pharmaceutical preparation according to claim 1, comprising 0.4-2% citric acid.

14. A process for the production of a solid pharmaceutical preparation according to claim 8, comprising suspending
(a) levothyroxine sodium and optionally liothyronine sodium in an aqueous gelatine solution,
(b) spraying the suspension obtained in (a) onto the filler in a fluidized bed granulation and drying to form granules, citric acid being either dissolved in the aqueous gelatine solution or admixed with the granules,
(c) collecting the granules obtained in (b) and optionally,
(d) mixing a disintegrant and optionally a lubricant with the granules obtained in (c), and
(e) compressing a mixture obtained in (d) to give tablets.

15. The process for the production of a solid pharmaceutical preparation according to claim 14, wherein an antioxidant is dissolved in the aqueous gelatine solution used in (a) or is admixed with the granules in (d).

16. The process for the preparation of a solid pharmaceutical preparation according to claim 14, wherein the granules or the tablets are provided with a coating.

17. A process for the stabilization of levothyroxine sodium, comprising adding to a composition of said levothyroxine sodium a stabilizing-effective amount of gelatine, citric acid and a filler that is sucrose, mannitol or lactose and maize starch, whereby said composition contains, by weight, based on the composition, 2-10% gelatine, 0.2-3% citric acid, 50-80% mannitol, sucrose or lactose and 10 to 30% maize starch.

18. The process according to claim 17, wherein the filler is mannitol and maize starch.

* * * * *